United States Patent [19]

Sigwart et al.

[11] Patent Number: 5,948,921
[45] Date of Patent: Sep. 7, 1999

[54] METHOD FOR THE SELECTIVE HYDROGENATION OF VINYL OXIRANE TO BUTYLENE OXIDE

[76] Inventors: Christoph Sigwart, Kurpfazstr. 9, 69198 Schriesheim; Klaus Harth, Starenweg 6, 67317 Altleiningen; Rolf Fischer, Bergstr.98, 69121 Heidelberg, all of Germany

[21] Appl. No.: 09/029,520

[22] PCT Filed: Aug. 29, 1996

[86] PCT No.: PCT/EP96/03799

§ 371 Date: Mar. 5, 1998

§ 102(e) Date: Mar. 5, 1998

[87] PCT Pub. No.: WO97/09321

PCT Pub. Date: Mar. 13, 1997

[30] Foreign Application Priority Data

Sep. 5, 1995 [DE] Germany ............................ 195 32 645

[51] Int. Cl.⁶ .................................................. C07D 301/02
[52] U.S. Cl. .............................................................. 549/540
[58] Field of Search ................................................ 549/540

[56] References Cited

U.S. PATENT DOCUMENTS

| | | | |
|---|---|---|---|
| 2,561,984 | 7/1951 | Hillyer et al. | 260/598 |
| 4,536,482 | 8/1985 | Carcia | 502/5 |
| 5,077,418 | 12/1991 | Falling | 549/540 |
| 5,117,013 | 5/1992 | Falloing | 549/540 |
| 5,559,065 | 9/1996 | Lauth et al. | 502/5 |
| 5,620,743 | 4/1997 | Harth et al. | 427/213 |

FOREIGN PATENT DOCUMENTS

| | | |
|---|---|---|
| 576944 | 6/1993 | European Pat. Off. . |
| 4407486 | 3/1994 | Germany . |

*Primary Examiner*—Ba K. Trinh

[57] ABSTRACT

1,2-Butylene oxide is prepared by catalytic hydrogenation of vinyloxirane over a heterogeneous catalyst produced by depositing one or more catalytically active elements of groups 7 to 11 of the Periodic Table of the Elements from the gas phase onto an inert, nonmetallic support.

7 Claims, No Drawings

METHOD FOR THE SELECTIVE HYDROGENATION OF VINYL OXIRANE TO BUTYLENE OXIDE

This application is a 371 of PCT/EP96/03799, dated Aug. 29, 1996.

The present invention relates to an improved process for preparing 1,2-butylene oxide by catalytic hydrogenation of vinyloxirane over heterogeneous catalysts.

The heterogeneous catalytic hydrogenation of vinyloxirane is known.

According to U.S. Pat. No. 2,561,984, the hydrogenation of vinyloxirane in ethanol over a palladium/activated carbon catalyst at 25° C./2 bar gives n-butyraldehyde as main product after a reaction time of 3 hours. In contrast, Raney nickel as catalyst results in formation of mainly n-butanol at 25° C. and 2 bar after a reaction time of 1.5 hours. Nothing is recorded about the formation of butylene oxide.

A paper by Aizikovich et al. (J. Gen. Chem. USSR, 28 (1958) 3076) describes the catalytic hydrogenation of vinyloxirane in methanol or ethanol over platinum, palladium and Raney nickel catalysts. A supported palladium catalyst (1.8% by weight of palladium on calcium carbonate) results in formation of mainly n-butanol at 15° C./1 bar. In this document, the most important intermediate in the hydrogenation is regarded as crotyl alcohol, although the formation of n-butyraldehyde is also observed. In this paper too, there is no reference to formation of 1,2-butylene oxide.

In U.S. Pat. No. 5,077,418 and U.S. Pat. No. 5,117,013 it is reported that the hydrogenation of vinyloxirane solutions over palladium-containing catalysts gives n-butyraldehyde as main product. Thus, hydrogenation of vinyloxirane together with tetrahydrofuran as solvent over a palladium/activated carbon catalyst (5% by weight of palladium on activated carbon) at from 50 to 55° C. and a pressure of 3.5 bar gives, after a reaction time of 3 hours, a hydrogenation product containing 55% of n-butyraldehyde, only 27% of 1,2-butylene oxide and 9% of n-butanol.

If the hydrogenation is carried out over supported catalysts containing palladium on aluminum oxide (5% Pd/$Al_2O_3$), only traces of 1,2-butylene oxide are formed after a reaction time of 6 hours at from 25 to 55° C. and a pressure of 3.5 bar or after a reaction time of 4 hours at 100° C. and a pressure of 20.7 bar. Quantitative conversion gives n-butyraldehyde as main product at a selectivity of 87% or 78%.

In addition, the hydrogenation of vinyloxirane over Raney nickel as hydrogenation catalyst at 50° C. and 3.5 bar is described, with 58% of n-butanol being formed as main product. The yield of 1,2-butylene oxide is, at 41%, low. In the hydrogenation of vinyloxirane over a supported platinum catalyst (1% by weight Pt/$Al_2O_3$) at 100° C. and a hydrogen pressure of 20.7 bar, only 40% of 1,2-butylene oxide together with 23% of n-butanol, 24% of various butenols, 5% of crotonaldehyde and 3% of n-butyraldehyde are found for complete conversion after a reaction time of 4.6 hours. Other platinum-containing catalysts given even lower 1,2-butylene oxide yields.

Furthermore, U.S. Pat. No. 5,077,418 and U.S. Pat. No. 5,117,013 teach that high 1,2-butylene oxide yields are only obtained using rhodium-containing catalysts. Varous supported rhodium catalysts (5% by weight of rhodium on activated carbon, 5% by weight of rhodium on aluminum oxide), which have a high content of the expensive noble metal rhodium, or hydrated rhodium oxide ($Rh_2O_3 \cdot xH_2O$) give 1,2-butylene oxide contents of 60–93% in the hydrogenation of vinyloxirane solutions. A disadvantage of this process is the low space-time yield based on the amount of rhodium used. Thus, the space-time yield in Example 2 of U.S. Pat. No. 5,117,013 is only 119 kg of 1,2-butylene oxide/kg Rh*h.

Neftekhimiya 33 (1993) 131 describes the hydrogenation of vinyloxirane over catalysts containing nickel, palladium and copper. Using Raney nickel or nickel on keiselguhr as catalyst, the hydrogenation proceeds primarily with opening of the epoxide ring which leads to predominant formation of 1-butenols and n-butanol. The yields of butylene oxide are low. For example, Raney nickel with methanol as solvent at 40° C./60 bar hydrogen pressure gives, after a reaction time of 20 min at a conversion of 94%, a reaction product which, based on reacted vinyloxirane, contains 89% of butenols, 8% of n-butanol and only 2% of 1,2-butylene oxide. The hydrogenation of vinyloxirane in methanol at 20° C./60 bar $H_2$ using freshly prepared Raney nickel (20% by weight) also gives, after a reaction time of 3 minutes at a conversion of 94%, only 9% of butylene oxide in addition to 79% of n-butanol and 6% of butenol. A hydrogenation experiment in methanol at 20° C./60 bar hydrogen pressure over a Raney nickel catalyst pretreated with isopropanol, nicotinic acid, pyridine and morpholine results, at 89% conversion, in the highest butylene oxide selectivity achievable using a nickel-containing catalyst, viz. 37%. At the same time, butenols and n-butanol are obtained in a selectivity of 56% and 9% respectively.

With palladium-containing catalysts, higher butylene oxide selectivities are achieved in the hydrogenation of vinyloxirane compared with the experiments using nickel-containing catalysts. For example, a palladium/activated carbon catalyst gives, without use of a solvent at 15° C./60 bar hydrogen pressure after a reaction time of 13 minutes at 61% conversion, 81% of butylene oxide based on vinyloxirane reacted. On the other hand, under the same reaction conditions but using methanol as solvent, a butylene oxide selectivity of only 53% is obtained at a conversion of 86%, with 13% of butanol and 18% of butenols being formed. A disadvantage of this process is that a high selectivity for the formation of 1,2-butylene oxide is achieved only at a relatively low partial conversion of the vinyloxirane. Since vinyloxirane and 1,2-butylene oxide are very difficult to separate from one another by distillation, this process is thus of no industrial importance. Palladium catalysts based on a polymer give, at a conversion of 68%, maximum butylene oxide selectivities of 60%, with butenols and n-butanol being formed in a selectivity of 18% and 4% respectively.

With copper-containing catalysts, a lower hydrogenation activity and resinification of the hydrogenation product is observed, making this process industrially impractical. At reaction temperatures of 60–100 ° C., 60 bar $H_2$ and 30% by weight of catalyst, a vinyloxirane conversion of 50% and a butylene oxide selectivity of 70% are achieved after a reaction time of 3 hours.

German Patent Application P 44 22 046.4 relates to catalysts produced by impregnation for use in the selective hydrogenation of vinyloxirane to give 1,2-butylene oxide. Despite the high selectivities described therein, relatively large amounts of butyraldehyde are formed as by-product.

German Patent Application P 44 07 486.7 teaches the hydrogenation of vinyloxirane over catalysts which are obtained by vapor deposition of the catalytically active elements on a support of metal foil or woven metal mesh. These catalysts make possible a highly selective conversion to the desired process product, but the supports used are relatively expensive.

It is an object of the present invention to find an economical process for preparing 1,2-butylene oxide from vinyloxirane in which 1,2-butylene oxide is formed in high yield and selectivity. A further object is to find catalysts for this purpose which, in comparison with the catalysts of the prior art, require significantly smaller amounts of expensive noble metals as catalyst component. Finally, a process is to be found in which use is made of catalysts which can be produced from inexpensive support materials.

We have found that these objects are achieved by a process for preparing 1,2-butylene oxide by catalytic hydrogenation of vinyloxirane over a heterogeneous catalyst wherein the catalyst used is produced by deposition of one or more catalytically active elements of groups 7 to 11 of the Periodic Table of the Elements from the gas phase onto an inert, nonmetallic support.

The process of the present invention surprisingly makes it possible to selectively hydrogenate the double bond of vinyloxirane in accordance with equation (1),

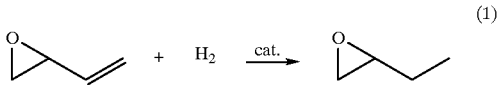

without the sensitive epoxide ring being hydrogenolytically opened to any appreciable extent during the hydrogenation and without appreciable occurrence of other secondary reactions, eg. isomerization of the vinyloxirane, for example to crotonaldehyde which is subsequently hydrogenated to give crotyl alcohol and butanol.

The catalysts used according to the present invention can be produced by depositing one or more elements of groups 7 to 11 of the Periodic Table of the Elements, which have previously also been referred to as transition groups I., VII. and VIII., in particular copper, rhenium, ruthenium, cobalt, nickel, palladium or platinum or mixtures of these elements onto a support, for example by physical vapor deposition (PVD) and/or chemical vapor deposition (CVD). Catalysts comprising palladium, cobalt, nickel, and also those comprising copper and nickel as active elements are particularly preferred.

PVD and CVD processes are described, for example, in R. F. Bhunshah et al, "Deposition Technologies for Films and Coatings", Noyes Publications, 1982. Suitable PVD processes are, for example, evaporating on, cathode atomization (sputtering) or electric arc coating, preferably cathode atomization. Known CVD processes are thermal CVD and plasma CVD.

In evaporating on, the coating material, ie. one or ore elements of groups 7 to 11 of the Periodic Table of the Elements, is introduced in a manner known per se into a suitable vapor source such as electrically heated vaporizer boats or electron beam vaporizers. The coating material, in general a metal or an alloy, is then heated under reduced pressure, usually in the range from $10^{-7}$ to $10^{-3}$ mbar, causing a part of the coating material to be vaporized and deposit on the substrate as a layer, ie. according to the invention on inert, nonmetallic supports. The range at which the layer is evaporated on can be controlled by means of the temperature of the vapor source.

In cathode atomization, the coating material is applied in solid form as target to the cathode of a plasma system, atomized under reduced pressure (preferably from $5\times10^{-4}$ to $1\times10^{-1}$ mbar) in a process gas atmosphere by application of a plasma and deposited on the support to be coated. The process gas usually contains a noble gas such as argon.

In electric arc coating, the coating material is removed from the source using an electric arc which leads to a high degree of ionization of the coating material in the process gas atmosphere. The support to be coated can be provided with a generally negative bias, which leads to an intensive ion bombardment during coating.

In CVD of the coatings of the present invention, a gas mixture comprising at least one sufficiently volatile organometallic starting compound of an element of groups 7 to 11 of the Periodic Table is introduced into the coating chamber and decomposed by introduction of thermal energy (thermal CVD) or under the action of a plasma (plasma CvD), with the desired coating being formed on the support. The gas mixture used can additionally contain inert gases such as He, Ne, Ar, Kr or Xe and further reactive gases. Deposition is carried out in a pressure range of from $10^{-4}$ to $10^{+3}$ mbar. Suitable starting compounds are, for example, carbonyl compounds, acetylacetonates and cyclopentadienyl compounds of the catalytically active elements.

For producing the coatings of the invention using the preferred method of cathode atomization, various method variants such as magnetron sputtering, DC or RF sputtering, bias sputtering or reactive sputtering and also combinations thereof are suitable. In magnetron sputtering, the target to be atomized is located in an external magnetic field which concentrates the plasma into the region of the target and thus effects an increase in the atomization range. In the case of DC or RF sputtering, the excitation of the atomization plasma is by means of a DC or an RF field. In bias sputtering, a generally negative bias is applied to the substrate to be coated, leading to an intensive bombardment of the substrate by ions during coating.

The setting of the coating thickness, the chemical composition and the microstructure of the coatings is carried out as described below by the coating parameters process gas pressure, atomization power, sputtering mode, substrate temperature and coating time.

Selection of appropriate sputtering powers and coating times enables the thickness of the sputtered layer to be conveniently selected from a few atomic layers to about 10 μm. For the process of the present invention, coating thicknesses of from 1 to 1000 nm are preferred.

Multicomponent active coatings can be produced by atomization of a suitable multicomponent target. Suitable targets are either homogeneous alloy targets which are produced in a known manner by melt processes or by powder metallurgical methods, or inhomogeneous mosaic targets which are produced by joining smaller sub-pieces of different chemical composition or by laying or gluing small disk-shaped pieces of material onto homogeneous targets. Alternatively, metallic alloys can be produced by simultaneously atomizing two or more targets of different composition (simultaneous sputtering).

Using the deposition processes specified, it is also conceivable to produce thin gradated coatings or multiple coatings whose composition is varied in a defined manner with increasing coating thickness by means of the process parameters mentioned.

The microstructure (eg. phase distribution, crystallite shape and size, crystallographic orientation, porosity) of the active coatings can likewise be controlled within wide limits by means of the process parameters specified. Thus, for example, magnetron atomization of a metal target in the pressure range from $4\times10^{-3}$ to $8\times10^{-3}$ mbar at coating thicknesses of from 20 to 500 nm leads to relatively dense and pore-free coatings, while above $10^{-2}$ mbar a column-shaped morphology with increasing porosity occurs. For coating thicknesses below about 50 nm, there is generally, depending on the roughness of the support, island growth of the coatings. In addition to the sputtering pressure and the support, the substrate temperature and the ion bombardment during coating influence the microstructure of the coatings. For the process of the present invention, preference is given in the case of Pd active coatings (20 nm) to, for example, a sputtering pressure of from 1 to $10\times10^{-2}$ mbar.

To achieve uniform coating of the support, it is necessary for the support materials to be kept in motion during the coating procedure using suitable mechanical or flow-mechanical apparatuses. Suitable mechanical apparatuses for this purpose are, for example, cages, drums, dishes or channels which are moved periodically and in which the supports to be coated are brought into random motion. Alternatively, it is conceivable that the supports to be coated are kept in random motion by means of a fluidized-bed process (cf. DE-A 43 40 480).

Suitable supports for the catalysts able to be used in the process of the present invention are, for example, shaped bodies of glass, quartz glass, ceramic, titanium dioxide, zirconium dioxide, aluminum oxide, aluminosilicates, borates, steatite, magnesium silicate, silicon dioxide, silicates, carbon, eg. graphite, or mixtures of the specified materials. Preference is given to steatite, silicon dioxide and aluminum oxide. The support can be porous or nonporous. Suitable shaped bodies are extrudates, pellets, wagon wheels, stars, monoliths, spheres, chippings or rings. Particular preference is given to spheres, pellets and extrudates. The selection of the shaped bodies is not restricted primarily by the method of production of the catalysts to be used according to the present invention, but by the way in which the desired catalyst is used, for example as suspension or fixed-bed catalyst. Thus, spheres can have a size of, for example, from 100 μm to 2 mm, extrudates can be from 1 to 5 mm thick and chippings can have a size of from 0.1 to 10 mm.

By means of the techniques described for depositing the catalytically active elements, it is possible to also apply promoters to the supports simultaneously or successively. Suitable promoters are primarily elements of group 4 of the Periodic Table of the Elements (formerly: transition group IV), in particular zirconium.

The catalysts thus produced can be used directly in the process of the present invention, but they are advantageously reduced prior to use in the process of the present invention, generally using hydrogen or hydrogen-containing gases at, typically, from 50 to 300° C., preferably from 80 to 250° C. The reduction is generally carried out until no more water is formed. This reaction can eliminate oxide or adsorbate layers formed during deposition or by reaction of the catalytically active elements with air. Hydrogen can be used diluted with inert gases such as $CO_2$, argon or nitrogen.

To carry out the process of the present invention, vinyloxirane or solutions of vinyloxirane in a solvent which is inert under the reaction conditions is hydrogenated in the presence of the catalysts to be used according to the present invention at generally from 0 to 200° C., preferably from 10 to 130° C., in particular from 20 to 100° C. and particularly preferably at from 25 to 60 ° C., at a pressure of generally from 1 to 300 bar, preferably from 1 to 100 bar and particularly preferably from 1 to 50 bar.

The process of the present invention can be carried out without solvent or advantageously in the presence of a solvent which is inert under the reaction conditions. Such solvents can be, for example: ethers such as tetrahydrofuran, dioxane, methyl tert-butyl ether, di-n-butyl ether, dimethoxyethane or diisopropyl ether, alcohols such as methanol, ethanol, propanol, isopropanol, n-butanol, isobutanol or tert-butanol, $C_2$–$C_4$-glycols, hydrocarbons such as petroleum ether, benzene, toluene or xylene, N-alkyllactams such as N-methylpyrrolidone or N-octylpyrrolidone.

The process of the present invention can be performed either continuously or batchwise. In the continuous procedure, it is advantageous, for example, to use tube reactors in which the catalyst is arranged as a fixed bed over which the reaction mixture can be passed in upflow or downflow mode. In the batchwise procedure, either simple stirred reactors or, advantageously, loop reactors can be used.

The work-up of the reaction mixture for isolating the 1,2-butylene oxide can be carried out in a conventional manner, eg. by distillation.

The vinyloxirane required as starting material can be prepared, for example, by the process of U.S. Pat. No. 4,897,498 by partial oxidation of 1,3-butadiene over silver catalysts.

1,2-Butylene oxide is used, for example, as fuel additive or as stabilizer for chlorinated hydrocarbons.

EXAMPLES

Example 1

Production of Catalysts by Cathode Atomization a) Production of Catalysts of the Present Invention The cathode atomization unit used was an Alcatel SCM 850 sputtering unit. Various supports in spherical form (eg. Table 1) were placed on a round steel mesh (diameter 150 mm) having a mesh opening of about 1 mm and introduced into a cathode atomization unit. A target corresponding to Table 1 was used at a distance of 70 mm and the unit was evacuated. Argon was then introduced up to a pressure corresponding to Table 1. By applying a suitable potential to the target, a coating was deposited on the support. During this procedure, the supports were moved randomly by mechanical agitation of the steel mesh so as to ensure homogeneous coatings. The results are shown in Table 1.

TABLE 1

| Cat. No. | Support material | Sphere size | Target | Power [W] | Sputtering pressure [mbar] | Coating thickness [nm] |
|---|---|---|---|---|---|---|
| 1 | Steatite | 2 mm | Pd | 250 (RF) | $5 \times 10^{-2}$ | 20 |
| 2 | Steatite | 2 mm | Pd | 250 (RF) | $1 \times 10^{-2}$ | 20 |
| 3 | Steatite | 2 mm | Pd | 250 (RF) | $5 \times 10^{-3}$ | 1 |
| 4 | Steatite | 2 mm | Pd | 250 (RF) | $5 \times 10^{-3}$ | 10 |
| 5 | Steatite | 2 mm | Pd | 500 (RF) | $5 \times 10^{-3}$ | 100 |
| 6 | Steatite | 2 mm | Pd | 500 (RF) | $5 \times 10^{-3}$ | 1000 |
| 7 | $SiO_2$ | 1.5–3.5 mm | Pd | 250 (RF) | $5 \times 10^{-3}$ | 20 |
| 8 | $Al_2O_3$ | 1.4–2.8 mm | Pd | 250 (RF) | $5 \times 10^{-3}$ | 20 |
| 9 | Glass | 2 mm | Pd | 500 (RF) | $5 \times 10^{-2}$ | 1000 |
| 10 | Steatite | 2 mm | $Ni_{30}Cu_{70}$* | 250 (DC) | $5 \times 10^{-2}$ | 10 |
| 11 | Steatite | 2 mm | $Ni_{20}Cu_{80}$* | 250 (DC) | $5 \times 10^{-2}$ | 20 |
| 12 | Steatite | 2 mm | $Ni_{30}Cu_{70}$* | 250 (DC) | $5 \times 10^{-2}$ | 100 |
| 13 | Steatite | 2 mm | Ni | 1000 (RF) | $5 \times 10^{-2}$ | 5 |
| 14 | Steatite | 2 mm | Co | 250 (DC) | $5 \times 10^{-2}$ | 10 |
| 15 | Steatite | 2 mm | Cu | 500 (DC) | $5 \times 10^{-2}$ | 10 |
| 16 | Steatite | 2 mm | Re | 500 (DC) | $5 \times 10^{-2}$ | 10 |
| 17 | Steatite | 2 mm | Ru | 500 (DC) | $5 \times 10^{-2}$ | 100 |

RF = RF potential;
DC = DC potential;
*mosaic target b) Production of catalysts containing Pd/Zr and Pt/Zr The catalysts shown in Table 2 were produced from amorphous alloys by cathode atomization, with one target ($Pd_1Zr_2$) being used for the catalyst No. 18 and 19 and two targets (Pt, Zr) being used for catalyst No. 20.

The catalysts No. 18 and 19 were subsequently further treated with a hydrogen/carbon dioxide mixture (14 l/h of $H_2$, 4 l/h of $CO_2$) at 280° C. for 24 hours.

The further treatment of catalyst No. 20 was carried out with a steam/nitrogen mixture (40 l/h of $N_2$, 3 g/l of $H_2O$) at 320° C. for 24 hours.

TABLE 2

| Cat. No. | Support material | Sphere size | Target 1 | Power 1 [W] | Target 2 | Power 2 [W] | Sputtering pressure [mbar] | Coating thickness [nm] |
|---|---|---|---|---|---|---|---|---|
| 18 | Steatite | 2 mm | $Pd_1Zr_2$ | 500 (RF) | — | — | $2.5 \times 10^{-2}$ | 1000 |
| 19 | Glass | 2 mm | $Pd_1Zr_2$ | 500 (RF) | — | — | $5 \times 10^{-2}$ | 300 |
| 20 | Steatite | 2 mm | Pt | 350 (RF) | Zr | 1000 (DC) | $5 \times 10^{-3}$ | 1000 |

Example 2

In an autoclave having a capacity of 50 ml, the solution to be hydrogenated comprising 2.5 g of vinyloxirane and 22.5 g of tetrahydrofuran was admixed with 0.5 g of catalyst No. 1 without prior activation with hydrogen and hydrogenated with hydrogen at 25° C. and 40 bar for 8 hours while stirring. At a conversion of 100%, 91.7 mol% of 1,2-butylene oxide, 1.0 mol% of n-butyraldehyde and 2.6 mol% of n-butanol were obtained. Examples 3–22

2.5 g of vinyloxirane in 22.5 g of tetrahydrofuran were hydrogenated with $H_2$ at 40 bar over the catalysts 2–20 using a method similar to that described in Example 2. Table 3 shows the reaction conditions and compositions of the hydrogenation products. The mol % figures are based on vinyloxirane reacted. If the catalysts were activated before use, this was carried out at 250° C. in a hydrogen atmosphere.

TABLE 3

| | Catalyst | | | | Reaction | VO | Composition of the reaction product [mol %] | | |
|---|---|---|---|---|---|---|---|---|---|
| | | Amount | | Temperature | time | conversion | | | |
| Ex. | No. | [g] | act. | [° C.] | [h] | [%] | BO | n-Ba | n-BuOH |
| 3 | 2 | 1 | + | 25 | 8 | 100 | 88.0 | 1.4 | 3.3 |
| 4 | 3 | 1 | − | 50 | 8 | 73 | 66.0 | 1.9 | 11.4 |
| 5 | 4 | 1 | − | 50 | 4 | 100 | 82.4 | 1.6 | 4.0 |
| 6 | 5 | 1 | − | 50 | 6 | 100 | 79.4 | 2.3 | 8.3 |
| 7 | 6 | 1 | − | 50 | 4 | 100 | 81.3 | 2.2 | 3.8 |
| 8 | 7 | 1 | + | 20 | 6 | 100 | 82.2 | 3.2 | 4.7 |
| 9 | 8 | 0.5 | − | 50 | 2 | 100 | 79.2 | 2.6 | 4.2 |
| 10 | 9 | 1 | + | 50 | 2 | 100 | 82.1 | 2.1 | 3.0 |
| 11 | 10 | 1 | + | 50 | 6 | 100 | 87.8 | 2.7 | 8.1 |
| 12 | 10 | 1 | + | 25 | 8 | 100 | 88.5 | 1.5 | 5.3 |
| 13 | 11 | 1 | + | 50 | 6 | 100 | 86.0 | 2.5 | 8.5 |
| 14 | 12 | 1 | + | 50 | 8 | 100 | 82.4 | 2.0 | 6.2 |
| 15 | 13 | 2 | + | 20 | 8 | 100 | 86.0 | 1.8 | 6.0 |
| 16 | 14 | 2 | + | 20 | 6 | 100 | 83.2 | 2.3 | 8.0 |
| 17 | 15 | 1 | + | 50 | 8 | 68 | 89.1 | 1.1 | 2.2 |
| 18 | 16 | 2 | + | 50 | 8 | 66 | 86.4 | 1.5 | 4.3 |
| 19 | 17 | 1 | + | 50 | 8 | 41 | 91.0 | 0.1 | 2.1 |
| 20 | 18 | 1 | + | 50 | 4 | 100 | 81.2 | 2.5 | 4.7 |
| 21 | 19 | 1 | + | 50 | 6 | 100 | 83.1 | 2.0 | 3.7 |
| 22 | 20 | 2 | + | 50 | 8 | 100 | 80.4 | 2.7 | 6.9 | act. = activated
VO = Vinyloxirane,
BO = 1,2-butylene oxide,
n-BA = n-butyraldehyde,
n-BuOH = n-butanol

We claim:

1. A process for preparing 1,2-butylene oxide by catalytic hydrogenation of vinyloxirane over a heterogeneous catalyst, wherein the catalyst used is produced by deposition of one or more catalytically active elements of groups 7 to 11 of the Periodic Table of the Elements from the gas phase onto an inert, nonmetallic support.

2. A process as claimed in claim 1, wherein the catalytically active elements used are palladium, cobalt, nickel or a mixture of copper and nickel.

3. A process as claimed in claim 1, wherein the inert support used is steatite, silicon dioxide or aluminum oxide.

4. A process as claimed in claim 1, wherein the ctalytically active elements are brought into the gas phase by cathode atomization.

5. A process as claimed in claim 1, wherein catlaysts having a layer thickness of the catalytically active elements of from 1 to 1000 nm are used.

6. A process as claimed in claim 1, wherein the catalysts are treated at from 50 to 300° C. with hydrogen prior to use.

7. A process as claimed in claim 1, wherein not only the catalytically active elements but also promoters from group 4 of the Periodic Table of the Elements are deposited from the gas phase onto the support.

* * * * *